United States Patent
Hagihara et al.

(10) Patent No.: US 10,443,037 B2
(45) Date of Patent: Oct. 15, 2019

(54) LONG-TERM CELL-CULTIVATION USING POLYIMIDE POROUS MEMBRANE AND CELL-CRYOPRESERVATION METHOD USING POLYIMIDE POROUS MEMBRANE

(71) Applicant: UBE INDUSTRIES, LTD., Ube-shi, Yamaguchi (JP)

(72) Inventors: Masahiko Hagihara, Ube-shi (JP); Motohisa Shimizu, Ube-shi (JP); Yukinori Wada, Ube-shi (JP)

(73) Assignee: UBE INDUSTRIES, LTD., Yamaguchi (JP)

(*) Notice: Subject to any disclaimer, the term of this patent is extended or adjusted under 35 U.S.C. 154(b) by 0 days.

(21) Appl. No.: 15/880,457

(22) Filed: Jan. 25, 2018

(65) Prior Publication Data

US 2018/0208887 A1    Jul. 26, 2018

Related U.S. Application Data

(62) Division of application No. 15/545,252, filed as application No. PCT/JP2016/052206 on Jan. 26, 2016.

(30) Foreign Application Priority Data

Jan. 26, 2015  (JP) ................. 2015-012537
Jan. 26, 2015  (JP) ................. 2015-012810

(51) Int. Cl.
*C12N 5/00* (2006.01)
*C08J 9/28* (2006.01)
(Continued)

(52) U.S. Cl.
CPC ......... *C12N 5/0068* (2013.01); *A01N 1/0231* (2013.01); *A01N 1/0236* (2013.01);
(Continued)

(58) Field of Classification Search
CPC .. C12N 5/0068; C12N 5/0686; C12N 5/0656; C12N 2533/30; A01N 1/0236;
(Continued)

(56) References Cited

U.S. PATENT DOCUMENTS 4,228,243 A   10/1980  Iizuka
7,041,343 B1  5/2006   Nelles et al.
(Continued)

FOREIGN PATENT DOCUMENTS

EP   1 864 641 A1   12/2007
EP   3 026 108 A1   6/2016
(Continued)

OTHER PUBLICATIONS

A. Sputtek. Cryopreservation of Red Blood Cells and Platelets. Ch. 20 in Methods in Molecular Biology (2007), v368, 2nd Ed., edited by Day and Stacey, eISBN: 1-59745-362-, p. 283-301 (Year: 2007).*

(Continued)

*Primary Examiner* — Sean C. Barron
(74) *Attorney, Agent, or Firm* — Mintz Levin Cohn Ferris Glovsky and Popeo PC

(57) ABSTRACT

The invention relates to a long term cell culturing method and a cell culturing apparatus and kit that employ a porous polyimide film. The invention further relates to a cell cryopreservation method and kit employing the porous polyimide film.

16 Claims, 9 Drawing Sheets

(51) Int. Cl.
| | |
|---|---|
| C12N 1/16 | (2006.01) |
| C12N 1/20 | (2006.01) |
| A01N 1/02 | (2006.01) |
| C12M 1/12 | (2006.01) |
| C08J 5/18 | (2006.01) |
| C08J 9/36 | (2006.01) |
| C12M 1/00 | (2006.01) |
| C12N 5/077 | (2010.01) |
| C12N 5/071 | (2010.01) |

(52) U.S. Cl.
CPC ......... *A01N 1/0268* (2013.01); *A01N 1/0284* (2013.01); *C08J 5/18* (2013.01); *C08J 9/28* (2013.01); *C08J 9/36* (2013.01); *C12M 25/02* (2013.01); *C12M 29/00* (2013.01); *C12N 1/16* (2013.01); *C12N 1/20* (2013.01); *C12N 5/00* (2013.01); *C12N 5/0656* (2013.01); *C12N 5/0686* (2013.01); *C08J 2379/08* (2013.01); *C12N 2533/30* (2013.01)

(58) Field of Classification Search
CPC ..... A01N 1/0284; C12M 29/00; C12M 25/02; C08J 9/36; C08J 5/18; C08J 2379/08
See application file for complete search history.

(56) References Cited

U.S. PATENT DOCUMENTS

| | | | |
|---|---|---|---|
| 2004/0058437 A1 | 3/2004 | Rodgers et al. | |
| 2005/0265980 A1* | 12/2005 | Chen .................. | C12N 5/0647 424/93.7 |
| 2011/0290112 A1 | 12/2011 | Liu et al. | |
| 2011/0318556 A1 | 12/2011 | Ohya et al. | |
| 2012/0207999 A1 | 8/2012 | Ohya et al. | |
| 2013/0045355 A1 | 2/2013 | Ohya et al. | |
| 2018/0208887 A1 | 7/2018 | Hagihara et al. | |

FOREIGN PATENT DOCUMENTS

| | | |
|---|---|---|
| JP | 63-196286 A | 8/1988 |
| JP | 63-198975 A | 8/1988 |
| JP | 63-198978 A | 8/1988 |
| JP | 05-123168 A | 5/1993 |
| JP | H0630570 B2 | 4/1994 |
| JP | 10-108673 A | 4/1998 |
| JP | 2002-034551 A | 2/2002 |
| JP | 2003-047464 A | 2/2003 |
| JP | 2003-524404 A | 8/2003 |
| JP | 2004-173563 A | 6/2004 |
| JP | 2005-536233 A | 12/2005 |
| JP | 2011-172533 A | 9/2011 |
| JP | 2011-219585 A | 11/2011 |
| JP | 2011-219586 A | 11/2011 |
| JP | 5140155 A | 2/2013 |
| WO | 2010/038873 A1 | 4/2010 |
| WO | WO-2011/125988 A1 | 10/2011 |
| WO | 2015/012415 A1 | 1/2015 |

OTHER PUBLICATIONS

Akkok et al. Use of different DMSO concentrations for cryopreservation of autologous peripheral blood stem cell grafts does not have any major impact on levels of leukocyte- and platelet-derived soluble factors . Cytotherapy (2009), v11(6), p. 749-760; (Year: 2009).*

Lutzow et al. Poly(ether imide) Scaffolds as Multifunctional Materials for Potential Applications in Regenerative Medicine. Artificial Organs (2006), v30(10), p. 764-769. (Year: 2006).*

Liu et al. Cryopreservation of human spermatozoa with minimal non-permeable cryoprotectant. Cryobiology (2016), v73, p. 162-167. (Year: 2016).*

Maenosono, Hirotaka et al., "A Transparent Polyimide Film as a Biological Cell Culture Sheet with Microstructures," *Journal of Biomaterials and Nanobiotechnology* (published online Jan. 2014; accepted Dec. 28, 2013); 5:17-23.

Ahern, Holl, "Hollow Fiber Bioreactor Systems Increase Cell Culture Yield," *The Scientist Magazine* (Feb. 19, 1990); 2 pages.

Kim, Jiseon et al., "Biological Characterization of Long-term Cultured Human Mesenchymal Stem Cells," *Arch Pharm Res.* (accepted Dec. 26, 2008); 32(1):117-126.

Kim, Jee Yon et al., "CHO cells in biotechnology for production of recombinant proteins: current stat and further potential," *Appl Microbiol Biotechnol* (2002; published online Dec. 9, 2011); 93:917-930.

International Search Report dated May 10, 2016 corresponding to International Patent Application No. PCT/JP/2016/052206, filed on Jan. 26, 2016; 2 pages.

Bissoyi, Akalabya et al., "Cryopreservation of hMSCs seeded silk nanofibers based tissue engineered constructs," *Cryobiology* (Apr. 20, 2014) 68:332-342.

Daoud, Jamal T. et al., "Long-term in vitro human pancreatic islet culture using three-dimensional microfabricated scaffolds," *Biomaterials* (2011; avail online Nov. 19, 2010); 32:1536-1542.

Kawakami, Hiroyoshi, "Cell Culture on Nano- or Micro-relief pattern Surface," *Membrane* (Jul. 10, 2007); 32(5):266-270 (see, English Abstract).

Julien, Sylvie et al., "Implantation of ultrathin, biofunctionalized polyimide membranes into the subretinal space of rats," *Bomaterials* (Mar. 8, 2011 online); 32:3890-3898.

Mortera-Blanco, Teresa et al., "Long-term cytokine-free expansion of cord blood mononuclear cells in three-dimensional scaffolds," *Biomaterials* (Sep. 9, 2011); 32:9263-9270.

Seifert, B. et al., "Polyetherimide: A New Membrane-Forming Polymer for Biomedical Applications," *Artificial Organs* (2002); 26(2):189-199.

Tao, Chun-Te et al., "Polyetherimide membrane formation by the cononsolvent system and its biocompatibility of MG63 cell line," *Journal of Membrane Science* (2006; accepted Jun. 10, 2005); 269:66-74.

* cited by examiner

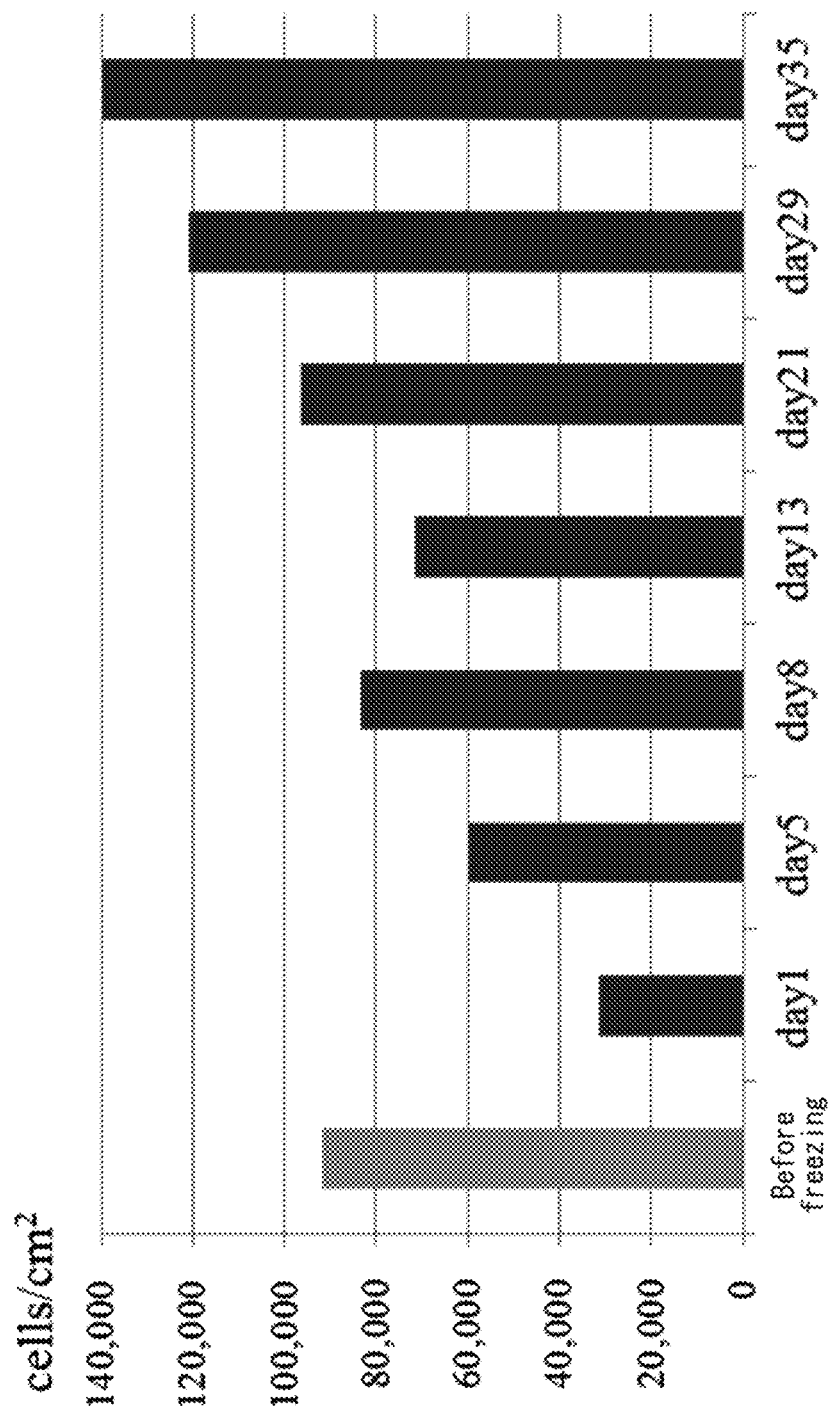

LONG-TERM CELL-CULTIVATION USING POLYIMIDE POROUS MEMBRANE AND CELL-CRYOPRESERVATION METHOD USING POLYIMIDE POROUS MEMBRANE

TECHNICAL FIELD

The present invention relates to a long term cell culturing method, and to a cell culturing apparatus and kit. More specifically, it relates to a long term cell culturing method and a cell culturing apparatus and kit that employ a porous polyimide film. The invention further relates to a cell cryopreservation method and kit. More specifically, it relates to a cell cryopreservation method and kit employing a porous polyimide film.

BACKGROUND ART

Cell Culturing

Cells generally exist as three-dimensional aggregates in the body, but in classical plate culturing, cells are cultured in a monolayer fashion with the cells attached to a vessel. A variety of culturing methods using culturing plates and the like have been developed in the past for culturing of adherent cells. When such plate culturing methods are carried out, the cultured cells continue their growth to a "confluent" state beyond which they are unable to grow, whereupon growth halts. A problem that occurs with many cells, though it depends on the type of cell, is that when the confluent state is continued without subculturing, spontaneous detachment of the cells begins after a certain period of time, making subculturing of the cells impossible.

With growing interest in cell grafting for regenerative medicine and cellular production of substances, there is an increasing demand for methods of culturing adherent cells. In the past, various three-dimensional culturing and support culturing systems have been developed, including pseudo-suspension culturing with supports such as microcarriers, spheroid culturing using modified surfaces, and hollow fiber culturing using hollow fibers as cell culture spaces. Hollow fiber culturing has been adopted as a methodology for steady-state and long term culturing of cells in an environment protected by strong hollow fibers, and many attempts are being made to achieve longer-term culturing by micro-carrier culturing as well, using air lift methods or device modifications designed to accomplish continuous culturing.

Such methodologies are intended to enlarge the space in which proliferation occurs by providing a three-dimensional environment in the growth space created by a support, in order to protect the support itself by a robust environment using device modifications or methodological modifications in the large growth space, and to allow prolonging of the culturing period. The systems that employ such methods require complex apparatuses or large-volume apparatuses, and in many cases they are closed systems in which it is difficult to add to the culturing environment itself once culturing has begun. Consequently, while a methodology is desired that would allow long term culturing of cells and convenient handling of the system, no suitable methodology has yet been developed.

On the other hand, investigation of the use of three-dimensional supports for long term cell culturing methods that mimic in vivo organs has been reported, as in NPLs 1 and 2. Such methods include experiments wherein reconstructed pancreatic islets of Langerhans are embedded in vivo, as well as long-term in vitro culturing of bone marrow cells, as examples of research aimed at site-selective reconstruction. These are important achievements that have demonstrated the importance and value of cell culturing in a three-dimensional environment for long term culturing, but since such supports are highly specific for a given purpose and the materials used have a fibrous structure composed of biocompatible materials, or a higher-order structure constructed by plotting, they have poor flexibility of use and also a lack of general handleability. It is desirable to develop a methodology that is convenient and can be applied to a variety of situations.

Cells are largely classified into two types, suspended cells and adherent cells, based on the features of their living form. Both types of cells, when provided for artificial culturing, are subjected to a cycle of cell seeding, culturing, proliferation, subculturing and frozen storage.

In recent years, with increasing interest being directed toward cultured cell-based production of vaccines and in vivo proteins such as enzymes, hormones, antibodies and cytokines, as well as cell grafts for use in regenerative medicine, advances continue to be made in the development of efficient and convenient methods for mass cell culturing. Cell culturing methods using supports have received special attention from the viewpoint of efficiency, as well as attractiveness and general utility, and a wide variety of methods continue to be developed. The general culturing of these cells is also being studied from multiple standpoints, also as relates to the techniques for cryopreservation of the cells. Beyond the classical freezing methods, there have been reported techniques that attempt to achieve freezing of cells more conveniently on the culture plate itself (PTL 4), methods aimed at improving survival rates of cells in freezing procedures by using three-dimensional supports (PTL 5), examples in which fibrous supports have been used to improve the cryopreservation properties of cultured cells (PTL 6), and examples of verifying the survival efficiency of stem cells (NPL 3).

The cryopreservation media, however, have been limited to fibrous materials with special structures, and such materials, while functioning as cryopreservation media, cannot be directly used as cell culture supports and have only been utilized for temporary preservation. There is a demand for establishment of a new methodology that allows thawing of cells from cryopreservation (cell arousal) to be carried out conveniently and efficiently, and in a consistent manner from use to re-freezing.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 7 to 9 describe porous polyimide films with numerous macro-voids, having excellent permeability for gases and the like, high porosity, excellent smoothness on both surfaces, relatively high strength and, despite high porosity, also excellent resistance against compression stress in the film thickness direction.

CITATION LIST

Patent Literature

[PTL 1] Japanese Unexamined Patent Publication HEI No. 5-123168
[PTL 2] Japanese Unexamined Patent Publication HEI No. 10-108673
[PTL 3] Japanese Examined Patent Publication HEI No. 6-30570
[PTL 4] Japanese Unexamined Patent Publication No. 2002-34551
[PTL 5] Japanese Patent No. 5140155
[PTL 6] Japanese Unexamined Patent Publication No. 2003-47464
[PTL 7] WO2010/038873
[PTL 8] Japanese Unexamined Patent Publication No. 2011-219585
[PTL 9] Japanese Unexamined Patent Publication No. 2011-219586

Non-Patent Literature

[NPL 1] Mortera-Blanco et al., Biomaterials 32 (2011) 9263-9270
[NPL 2] Daoud et al., Biomaterials 32 (2011) 1536-1542
[NPL 3] A. Bissoyi et al./Cryobiology 68 (2014) 332-342

DISCLOSURE OF THE INVENTION

Problems to be Solved by the Invention

It is an object of the present invention to provide a cell culturing method that allows convenient and stable long term culturing of cells to be carried out in a manner conforming to the necessary conditions and embodiments, and that is also adaptable in response to changes during culturing, as well as a cell culturing apparatus and kit for use in the culturing method.

It is another object of the invention to provide a cell freezing method that allows thawing of cells from cryopreservation (cell arousal) to be carried out conveniently and efficiently in a consistent manner from use to re-freezing.

Means for Solving the Problems

The present inventors have found that cells can be efficiently cultured for long periods by conducting the cell culturing using a porous polyimide film.

The present invention preferably includes, but is not limited to, the following modes.

[Mode 1]
A long term cell culturing method including:
(1) applying cells to a porous polyimide film, and
(2) applying the porous polyimide film to which the cells have been applied, to a cell culture medium and culturing the cells for 30 days or longer.

[Mode 2]
The method according to mode 1, wherein the cells are cultured for 60 days or longer in step (2).

[Mode 3]
The method according to mode 1, wherein the cells are cultured for 120 days or longer in step (2).

[Mode 4]
The method according to any one of modes 1 to 3, using two or more porous polyimide films layered either above and below or left and right in the cell culture medium.

[Mode 5]
The method according to any one of modes 1 to 4, wherein the porous polyimide films are:
i) folded,
ii) wound into a roll,
iii) connected as sheets or fragments by a filamentous structure, or
iv) bound into a rope,
and used by suspension or anchoring in the cell culture medium in the cell culturing vessel.

[Mode 6]
The method according to any one of modes 1 to 5, wherein in the culturing of step (2), all or some of the porous polyimide films are not in contact with the liquid phase of the cell culture medium.

[Mode 7]
The method according to any one of modes 1 to 6, wherein in the culturing of step (2), the total volume of the cell culture medium in the cell culturing vessel is 10,000 times or less of the total sum of the porous polyimide film volume including the cell survival zone.

[Mode 8]
The method according to any one of modes 1 to 7, wherein in the culturing of step (2), the total volume of the cell culture medium in the cell culturing vessel is 100 times or less of the total sum of the porous polyimide film volume including the cell survival zone.

[Mode 9]
The method according to any one of modes 1 to 8, wherein the culturing in step (2) is carried out in a system in which a cell culture medium is continuously or intermittently supplied to a cell culturing vessel from cell culture medium supply means installed outside of the cell culturing vessel.

[Mode 10]
The method according to mode 9, wherein the cell culture medium is circulated between the cell culture medium supply means and the cell culturing vessel.

[Mode 11]
The method according to mode 9 or 10, wherein the system is a cell culturing apparatus including a culturing unit which is the cell culturing vessel, and a culture medium-supply unit which is the cell culture medium supply means, wherein
the culturing unit is a culturing unit that houses one or more porous polyimide films to support cells, and that comprises a culture medium supply port and a culture medium discharge port, and
the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

[Mode 12]
The method according to mode 13, wherein the culturing unit is a culturing unit that does not comprise an air supply port, an air discharge port and an oxygen exchange membrane.

[Mode 13]
The method according to mode 11 or 12, wherein the culturing unit further comprises a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

[Mode 14]

The method according to any one of modes 1 to 13, wherein the cells are selected from the group consisting of animal cells, insect cells, plant cells, yeast cells and bacteria.

[Mode 15]

The method according to mode 14, wherein the animal cells are cells derived from an animal belonging to the subphylum Vertebrata.

[Mode 16]

The method according to mode 15, wherein the cells are selected from the group consisting of CHO cells, CHO-K1 cell lines, CHO DP-12 cell lines, CHO cell-related lines, Vero cells and MDCK cells.

[Mode 17]

The method according to any one of modes 1 to 16, wherein the porous polyimide film is a porous polyimide film including a polyimide obtained from a tetracarboxylic dianhydride and a diamine.

[Mode 18]

The method according to mode 17, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 19]

A cell culturing apparatus for use in the method according to any one of modes 1 to 18, including a porous polyimide film.

[Mode 20]

A cell culturing apparatus according to mode 19, wherein two or more porous polyimide films are layered either above and below or left and right.

[Mode 21]

A kit for use in the method according to any one of modes 1 to 13, including a porous polyimide film.

[Mode 22]

The use of a porous polyimide film for a long term cell culturing method.

[Mode 23]

A cell cryopreservation method, including:

(1) a step of supporting cells on a porous polyimide film, (2) a step of placing the cell-supporting porous polyimide film under conditions in which the cells freeze, to freeze the cells supported on the porous polyimide film, and (3) a step of storing the cell-supporting porous polyimide film under conditions in which the frozen state is maintained.

[Mode 24]

The method according to mode 23, wherein in step (1), the cells are seeded on the porous polyimide film to support the cells on the porous polyimide film.

[Mode 25]

The method according to mode 23, wherein in step (1), the cells are seeded and cultured on the porous polyimide film to support the cells on the porous polyimide film.

[Mode 26]

The method according to any one of modes 23 to 25, which further includes, following step (3), (4) a step of placing the cell-supporting porous polyimide film under conditions in which the cells thaw, to thaw the cells supported on the porous polyimide film.

[Mode 27]

The method according to mode 26, which further includes, following step (4), (5) a step of applying the cell-thawed porous polyimide film to a cell culture medium and culturing the cells.

[Mode 28]

The method according to mode 27, wherein in step (5), the cells are cultured until the cultured cells proliferate even outside of the porous polyimide film.

[Mode 29]

The method according to mode 27 or 28, wherein in step (5), the one or more separate non-cell-supporting porous polyimide films are applied onto the cell culture medium together with the cell-thawed porous polyimide film, and culturing is carried out to support the cells on the one or more separate porous polyimide films.

[Mode 30]

The method according to any one of modes 27 to 29, which further includes, following step (5), (6) a step of placing all or a portion of the cell-supporting porous polyimide film under conditions in which the cells freeze, to freeze the cells supported on the porous polyimide film, and (7) a step of storing the cell-supporting porous polyimide film under conditions in which the frozen state is maintained.

[Mode 31]

The method according to mode 30, wherein steps (1) to (7) are repeated several times.

[Mode 32]

The method according to any one of modes 23 to 31, wherein the cells are selected from the group consisting of animal cells, insect cells, plant cells, yeast cells and bacteria.

[Mode 33]

The method according to mode 32, wherein the animal cells are cells derived from an animal belonging to the subphylum Vertebrata.

[Mode 34]

The method according to mode 32 or 33, wherein the cells are adherent cells.

[Mode 35]

The method according to mode 32 or 33, wherein the cells are suspension cells.

[Mode 36]

The method according to any one of modes 23 to 35, wherein the porous polyimide film is a porous polyimide film including a polyimide obtained from a tetracarboxylic dianhydride and a diamine.

[Mode 37]

The method according to mode 36, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 38]

The method according to mode 36 or 37, wherein the porous polyimide film is a porous polyimide film with a multilayer structure, having two different surface layers and a macro-void layer.

[Mode 39]

A porous polyimide film for cryopreservation of cells.

[Mode 40]

A porous polyimide film to be used in the method according to any one of modes 23 to 28.

[Mode 41]

A kit for use in the method according to any one of modes 23 to 38, including a porous polyimide film.

[Mode 42]

The use of a porous polyimide film for the method according to any one of modes 23 to 38.

Effect of the Invention

The present invention allows convenient and stable long term culturing of cells to be performed using a porous polyimide film. According to the invention, the porous polyimide film that is to serve as the culture support has large diameter communicating pores through which cells can pass, and the three-dimensional space is ensured at the final stage even when very large volumes of cells are growing in the space. Hence, there is less likelihood of a limit to the culturing period such as occurs in a confluent state in classical plate culturing. Moreover, according to the invention there is no particular need for pretreatment of the porous polyimide film by collagen or the like during the cell culturing. Furthermore, since the porous polyimide film is a flexible thin-film material, bending, folding or cutting into a free shape is more convenient. Consequently, the porous polyimide film including the cells can be removed out as necessary at any time throughout the culturing and provided for processing or measurement. It is also suitable for automation of cell culturing. In addition, since the porous polyimide film is a material with very high heat resistance, operations such as sterilization can be carried out in a very convenient manner.

By using the porous polyimide film for freezing of cells, it is possible to cryopreserve large volumes of cells and efficiently utilize the cells. After thawing from the frozen state, the cell culturing can be directly continued on the porous polyimide film. Moreover, the porous polyimide film on which cell culturing is continued may be contacted with another support such as a porous polyimide film on which cells are not growing, or placed in its vicinity to allow migration and proliferation of the cells. After migration of the cells is complete, the original porous polyimide film may be removed out and re-frozen, and stored for subsequent use. Thus, the series of procedures from cell arousal to use and freezing can be carried out with the same material. Since the process does not require complicated operations such as cell detachment with trypsin or the like or collagen coating, the process is convenient and efficient, and the procedures can be carried out rapidly. The method of the invention is also suitable for uses that include automated steps. In terms of efficiency as well, since it is possible to grow large volumes of cells in very thin films of at least 25 micrometers, the efficiency per unit volume is of a level hitherto unseen. For example, when a substance has been produced using a promising cell line, the cell line can be used for a prolonged period and directly frozen to preserve the cells, and then reused at the necessary time. A library of the promising cell line can also be easily prepared.

BRIEF DESCRIPTION OF THE DRAWINGS

FIG. 11 shows results for freezing and then thawing and culturing of human skin fibroblasts using a porous polyimide film.

MODE FOR CARRYING OUT THE INVENTION

I. Cell Culturing Method

Figure 1:
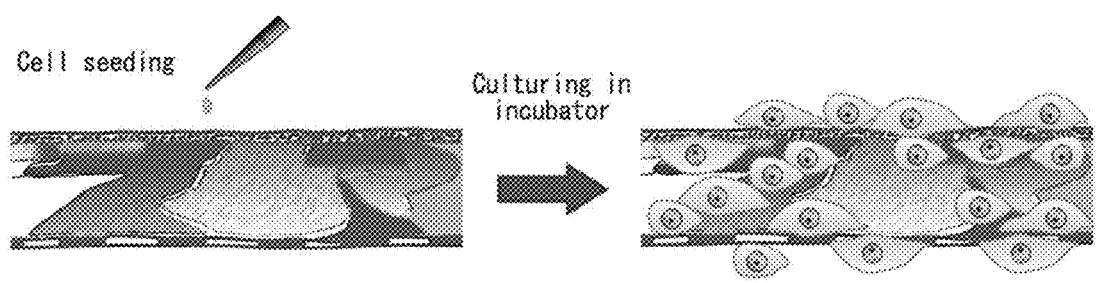
FIG. 1 is a model diagram of cell culturing using a porous polyimide film.

The present invention relates to a long term cell culturing method. The entire content of International Application Number PCT/JP2014/070407 is incorporated herein by reference.

The cell culturing method of the invention includes applying cells to a porous polyimide film and culturing them. The present inventors have found that a porous polyimide film is suitable for adhesion and culturing of cells, and have thereupon completed this invention. The method of the invention includes applying cells to a porous polyimide film and culturing the cells on the surface or in the interior of the polyimide film.

1. Application of Cells to Porous Polyimide Film

There are no particular restrictions on the specific steps for application of the cells to the porous polyimide film. It is possible to carry out the steps described throughout the present specification, or to employ any desired method suited for applying cells to a film-like support. Application of cells to the porous polyimide film in the method of the invention includes, but is not limited to, the following modes.

(A) A mode including a step of seeding cells on the surface of a porous polyimide film;

(B) A mode including a step of:

placing a cell suspension on the dried surface of the porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of the porous polyimide film with a cell culture solution or a sterilized liquid, loading a cell suspension into the wetted porous polyimide film, and retaining the cells in the cell suspension inside the film and allowing the water to flow out.

Mode (A) includes a step of directly seeding cells or a cell mass on the surface of a porous polyimide film. Alternatively, it includes a mode of placing a porous polyimide film in a cell suspension and wetting the cell culture solution from the surface of the film.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

For mode (B), a cell suspension is placed on the dried surface of a porous polyimide film. The porous polyimide film is allowed to stand, or the porous polyimide film is moved to promote efflux of the liquid, or part of the surface is stimulated to cause absorption of the cell suspension into the film, so that the cell suspension permeates into the film. While it is not our intention to be constrained by theory, this is believed to be due to the properties of each of the surface forms of the porous polyimide film. According to this mode, the cells are absorbed and seeded in the locations of the film where the cell suspension has been loaded.

Alternatively, as according to mode (C), after all or a portion of one or both sides of the porous polyimide film has been wetted with the cell culture solution or sterilized liquid, the cell suspension may be loaded into the wetted porous polyimide film. This will significantly increase the transit rate of the cell suspension.

For example, a method of wetting a portion of the film edges, for the main purpose of preventing fly loss of the film, may be used (hereunder referred to as "single-point wetting method"). The single-point wetting method is nearly the same as the dry method (mode (B)) in which the film essentially is not wetted. However, it is possible that cell solution permeation through the film is more rapid at the small wetted portions. There may also be used a method in which all of one or both sides of the porous polyimide film that have been thoroughly wetted (hereunder this will also be referred to as "wet film") is loaded with a cell suspension (this will hereunder be referred to as "wet film method"). In this case, the entire porous polyimide film has a greatly increased transit rate for the cell suspension.

According to modes (B) and (C), the cells in the cell suspension are retained in the film, while the water flows out. This allows treatment such as increasing the concentration of cells in the cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
|---|---|---|
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (−) | 7.4 | 7.4 |

In the method of the invention, application of cells to the porous polyimide film further includes a mode of adding adherent cells in a floating state as a suspension together with the porous polyimide film, to adhere the cells with the film (entangling). For example, for application of the cells to the porous polyimide film in the cell culturing method of the invention, the cell culture medium, the cells and one or more of the porous polyimide films may be placed in the cell culturing vessel. When the cell culture medium is a liquid, the porous polyimide film is in a floating state in the cell culture medium. The cells can adhere to the porous polyimide film due to the properties of the porous polyimide film. Thus, even with cells that are not suited for natural suspension culture, the porous polyimide film allows culturing in a floating state in the cell culture medium. The cells preferably spontaneously adhere to the porous polyimide film. Here, "adhere spontaneously" means that the cells are retained on the surface or in the interior of the porous polyimide film without applying any particular exterior physical or chemical force.

Cell culturing can be classified into culturing where the cultured cells are adhesion culture-type cells or suspension culture-type cells, depending on the state in the cell culture. Adhesion culture-type cells are cultured cells that adhere and grow on a culturing vessel, with the medium being exchanged at the time of subculture. Suspension culture-type cells are cultured cells that grow in a suspended state in a medium, and generally the medium is not exchanged with each subculture but dilution culture is carried out. Because suspension culture allows culturing in a suspended state, i.e. in a liquid, mass culturing becomes possible, and because it is three-dimensional culturing, unlike with adherent cells that grow only on the culturing vessel surface, the advantage of increased culturable cell count per unit space is afforded.

In the long term culturing method of the invention, when the porous polyimide film is used in a state suspended in the cell culture medium, two or more fragments of the porous polyimide film may be used. Since the porous polyimide film is a flexible thin-film, using such fragments that are suspended in the culture solution, for example, allows a porous polyimide film with a large surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example.

The sizes and shapes of the porous polyimide film fragments are not particularly restricted. The shapes may be as desired, such as circular, elliptical, quadrilateral, triangular, polygonal or string-like.

Because the porous polyimide film of the invention is flexible, it can be used with varying shapes. Instead of a flat form, the porous polyimide film can also be used by working into a three-dimensional shape. For example, porous polyimide films may be: i) folded, ii) wound into a roll, iii) connected as sheets or fragments by a filamentous structure, or iv) bound into a rope, for suspension or fixing in the cell culture medium in the cell culturing vessel. By forming into shapes such as i) to iv), it is possible to place a large amount of porous polyimide films into a fixed volume of cell culture medium, similar to using fragments. Furthermore, since each fragment can be treated as an aggregate, it is possible to aggregate and move the cell masses together, for overall high applicability.

With the same concept as fragment aggregates, two or more porous polyimide films may be used in a layered form either above and below or left and right in the cell culture medium. Layering includes a mode in which portions of the porous polyimide films overlap. Layered culturing allows culturing of cells at high density in a narrow space. It is also possible to further layer a film on the film on which cells are already growing, having it set thereover to create a multilayer of different cell types. The number of layered porous polyimide films is not particularly restricted.

Two or even more forms of the cell culturing method of the invention described above may be used in combination. For example, using any of the methods of modes (A) to (C), first the cells may be applied to the porous polyimide film and then the cell-adhered porous polyimide film may be used for suspension culture. Alternatively, the step of application to the porous polyimide film may be a combination of two or more of the methods of any of modes (A) to (C).

In the long term culturing method of the invention, preferably the cells grow and proliferate on the surface or in the interior of the porous polyimide film.

With the long term culturing method of the invention it is possible to carry out culturing of cells over a prolonged period of 30 days or longer, 60 days or longer, 120 days or longer, 200 days or longer or 300 days or longer, without subculturing procedures by trypsin treatment or the like as in the prior art. Moreover, with the long term culturing method of the invention, it is possible to culture cells for longer than the possible culturing period by conventional plate culture, such as a period of 1.5 times or longer, 2 times or longer, 2.5 times or longer, 3 times or longer, 3.5 times or longer, 4 times or longer or 4.5 times or longer, compared to the plate culture period. According to the invention, it is possible to maintain cells that have been generated by prolonged culturing by plate culture using a plate, in a dynamic live state for prolonged periods without causing detachment or death of the cells. According to the invention, even cells that have undergone long term culturing have virtually no change in cell viability or cell qualities (for example, differentiation-inducing efficiency, cell surface marker expression levels, etc.) compared to the cells before long term culturing. According to the invention, since the cells grow three-dimensionally in a porous polyimide film, they are less likely to have a culturing region limit as with conventional plate culturing, or to encounter contact inhibition that occurs on flat environments, thereby allowing cultured growth for prolonged periods. Moreover, according to the invention, it is possible to arbitrarily increase the cell culturing space by contacting a separate porous polyimide film with the cell-adhered porous polyimide film, allowing prolonged cultured growth while avoiding confluency that results in contact inhibition, without carrying out subculturing procedures with trypsin treatment as in the prior art. In addition, according to the invention there is provided a new storage method whereby the cells are stored for prolonged periods in a live state without freezing.

2. Cells

There are no particular restrictions on the type of cells that can be utilized for the method of the invention, and it may be used for growth of any type of cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, *E. coli, Bacillus subtilis* and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), MDCK cells (from canine renal tubular epithelial cells) and HepG2 cells (from human hepatic cancer). The term "transformants" refers to cells with an altered genetic nature by extracellularly introduced nucleic acid (DNA and the like). Suitable methods are known for transformation of animal cells, plant cells and bacteria.

3. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

This also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

For the purpose of the invention, a coloring precursor is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C. or higher, preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when heating, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(3-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl) isopropyl]benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl] sulfide, bis[3-(4-aminophenoxy)phenyl] sulfide, bis[4-(3-aminophenoxy)phenyl] sulfide, bis[4-(4-aminophenoxy)phenyl] sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film of the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the method of the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 µm in the planar direction of the film, surrounded by the partition and the surface layers (A-surface and B-surface), wherein the macro-void layer partition and the surface layers (A-surface and B-surface) each have thicknesses of 0.01 to 20 µm, with a plurality of pores with mean pore sizes of 0.01 to 100 µm, the pores being optionally communicating with each other, and also having a partial or total multilayer structure in communication with the macro-voids, where the total film thickness is 5 to 500 µm and the porosity is 40% or greater and less than 95%.

The total film thickness of the porous polyimide film used for the invention is not limited, but may be 20 to 75 µm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 µm, 0.01 µm to 40 µm, 0.01 µm to 30 µm, 0.01 µm to 20 µm or 0.01 µm to 15 µm, and the mean pore size of the holes in the B-surface being 20 µm to 100 µm, 30 µm to 100 µm, 40 µm to 100 µm, 50 µm to 100 µm or 60 µm to 100 µm. Most preferably, the A-surface of the porous polyimide film is a mesh structure having small holes with a mean pore size of no greater than 15 µm, such as 0.01 µm to 15 µm, and the B-surface is a large-hole structure with a mean pore size of 20 µm or greater, such as 20 µm to 100 µm.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

$$\text{Mean pore size} = 2 \times \sqrt{(Sa/\pi)} \quad (1)$$

(wherein Sa represents the average value for the pore areas)

The porosity of the porous polyimide film used for the invention can be determined by measuring the film thickness and mass of the porous film cut out to a prescribed size, and performing calculation from the basis weight according to the following formula (2).

$$\text{Porosity (\%)} = (1 - w/(S \times d \times D)) \times 100 \quad (2)$$

(wherein S represents the area of the porous film, d represents the total film thickness, w represents the measured mass, and D represents the polyimide density, the polyimide density being defined as 1.34 g/cm$^3$.)

For example, the porous polyimide films described in International Patent Publication No. WO2010/038873, Japanese Unexamined Patent Publication No. 2011-219585 and Japanese Unexamined Patent Publication No. 2011-219586 may also be used in the method of the invention.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cells.

Naturally, the porous polyimide film to which cells are applied in the method of the invention is preferably in a state including no cells other than those that are to be applied, i.e. a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a disinfectant such as ethanol, or electromagnetic wave sterilization using ultraviolet rays or gamma rays.

4. Cell Culturing and Culturing Volume

FIG. 1 shows a model diagram of cell culturing using a porous polyimide film. In the method of the invention, it is possible to culture large volumes of cells while drastically reducing the amount of medium used for cell culturing compared to the prior art. For example, large volumes of cells can be cultured for prolonged periods, even when all or a portion of the porous polyimide film is not in contact with the liquid phase of the cell culture medium. Also, the total volume of the cell culture medium in the cell culturing vessel, with respect to the total porous polyimide film volume including the cell survival zone, can be significantly reduced.

Throughout the present specification, the volume of the porous polyimide film without cells, occupying the space including the volume between the interior gaps, will be referred to as the "apparent porous polyimide film volume" (the state shown at the left in FIG. 1). In the state where the cells are applied to the porous polyimide film and the cells have been supported on the surface and the interior of the porous polyimide film, the total volume of the porous polyimide film, the cells and the medium that has wetted the porous polyimide film interior, which is occupying the space therein, will be referred to as the "porous polyimide film volume including the cell survival zone" (the state shown at the right in FIG. 1). When the porous polyimide film has a film thickness of 25 μm, the porous polyimide film volume including the cell survival zone is a value of at maximum about 50% larger than the apparent porous polyimide film volume. In the method of the invention, a plurality of porous polyimide films may be housed in a single cell culturing vessel for culturing, in which case the total sum of the porous polyimide film volume including the cell survival zone for each of the plurality of porous polyimide films supporting the cells may be referred to simply as the "total sum of the porous polyimide film volume including the cell survival zone".

Using the method of the invention, cells can be satisfactorily cultured for prolonged periods even under conditions in which the total volume of the cell culture medium in the cell culturing vessel is 10,000 times or less of the total sum of the porous polyimide film volume including the cell survival zone. Moreover, cells can be satisfactorily cultured for prolonged periods even under conditions in which the total volume of the cell culture medium in the cell culturing vessel is 1000 times or less of the total sum of the porous polyimide film volume including the cell survival zone. Cells can also be satisfactorily cultured for prolonged periods even under conditions in which the total volume of the cell culture medium in the cell culturing vessel is 100 times or less of the total sum of the porous polyimide film volume including the cell survival zone. In addition, cells can be satisfactorily cultured for prolonged periods even under conditions in which the total volume of the cell culture medium in the cell culturing vessel is 10 times or less of the total sum of the porous polyimide film volume including the cell survival zone.

In other words, according to the invention the space (vessel) used for cell culturing can be reduced to an absolute minimum, compared to a cell culturing apparatus in which conventional two-dimensional culturing is carried out. Furthermore, when it is desired to increase the number of cells cultured, the cell culturing volume can be flexibly increased by a convenient procedure including increasing the number of layered porous polyimide films. In a cell culturing apparatus comprising a porous polyimide film to be used for the invention, the space (vessel) in which cells are cultured and the space (vessel) in which the cell culture medium is stored can be separate, and the necessary amount of cell culture medium can be prepared according to the number of cells to be cultured. The space (vessel) in which the cell culture medium is stored can be increased or decreased according to the purpose, or it may be a replaceable vessel, with no particular restrictions. The concept of integration is important for freezing, as it allows freezing and storage of a large volume of cells in a minimal space.

The method used for counting the number of cells during or after culturing may be any of the known methods. For example, any publicly known method may be used to count the number of cells in the cell culturing vessel after culturing using the porous polyimide film, when the cells are evenly dispersed in the cell culture medium in the cell culturing vessel. For example, a cell counting method using CCK8 may be suitably used, as in the method employed in Example 1. Specifically, a Cell Counting Kit 8, as a solution reagent by Dojindo Laboratories (hereunder referred to as "CCK8") may be used to count the number of cells in ordinary culturing without using a porous polyimide film, and the correlation coefficient between the absorbance and the actual cell count determined. After then applying the cells, the cultured porous polyimide film may be transferred to CCK8-containing medium and stored in an incubator of 1 to 3 hours, and then the supernatant extracted and its absorbance measured at a wavelength of 480 nm, and the cell count determined from the previously calculated correlation coefficient.

3. Cell Culturing System and Culturing Conditions

In the method of the invention, the cell culturing system and culturing conditions may be set as appropriate according to the type of cells used. Culturing methods suited for various cells including animal cells, plant cells and bacteria are publicly known, and a person skilled in the art may carry out culturing of cells suited for the porous polyimide film, using any publicly known method. The cell culture medium may also be prepared as appropriate for the type of cells.

Cell culture methods and cell culture media for animal cells may be found in the Cell Culture Media Catalog of Lonza Group, Ltd., for example. Cell culture methods and cell culture media for plant cells may also be found in the Plant Tissue Culturing Media Series by Wako Corp., for example. Cell culture methods and cell culture media for bacteria may also be found in the General Bacterial Media Catalog of BD Corp., for example. The cell culture medium to be used in the method of the invention may be in any form such as a liquid medium, semi-solid medium or solid medium. Also, a liquid medium in droplet form may be sprayed into the cell culturing vessel to contact the medium with the cell-supporting porous polyimide film.

The cell culture using a porous polyimide film may also be combined with another suspension culture support such as a microcarrier, cellulose sponge or the like.

The method of the invention is not particularly restricted in terms of the form and scale of the system used for the culturing, and any scale from cell culturing dish to a flask, plastic bag, test tube or large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

The culturing in the method of the invention may be carried out in a manner with continuous circulation such as continuous addition and recovery of the medium on the porous polyimide film, or exposure of the porous polyimide film sheet to air using an open apparatus.

Cell culturing according to the invention may be carried out in a system in which a cell culture medium is continuously or intermittently supplied to a cell culturing vessel from cell culture medium supply means installed outside of the cell culturing vessel. The system may be such that the cell culture medium is circulated between the cell culture medium supply means and the cell culturing vessel.

When the cell culturing is to be carried out in a system in which the cell culture medium is continuously or intermittently supplied to the cell culturing vessel from cell culture medium supply means installed outside of the cell culturing vessel, the system may be a cell culturing apparatus including a culturing unit which is the cell culturing vessel, and a culture medium-supply unit which is the cell culture medium supply means, wherein the culturing unit is a culturing unit that houses one or more porous polyimide films to support cells, and that comprises a culture medium supply port and a culture medium discharge port, and the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

The culturing unit in the cell culturing apparatus may be a culturing unit that does not comprise an air supply port, an air discharge port and an oxygen exchange membrane, or it may be a culturing unit that comprises an air supply port and an air discharge port, or an oxygen exchange membrane. Even if the culturing unit does not comprise an air supply port, and an air discharge port and an oxygen exchange membrane, the oxygen, etc. necessary for cell culturing will be adequately supplied to the cells through the medium. Furthermore, in the cell culturing apparatus described above, the culturing unit may further comprise a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

Figure 2:
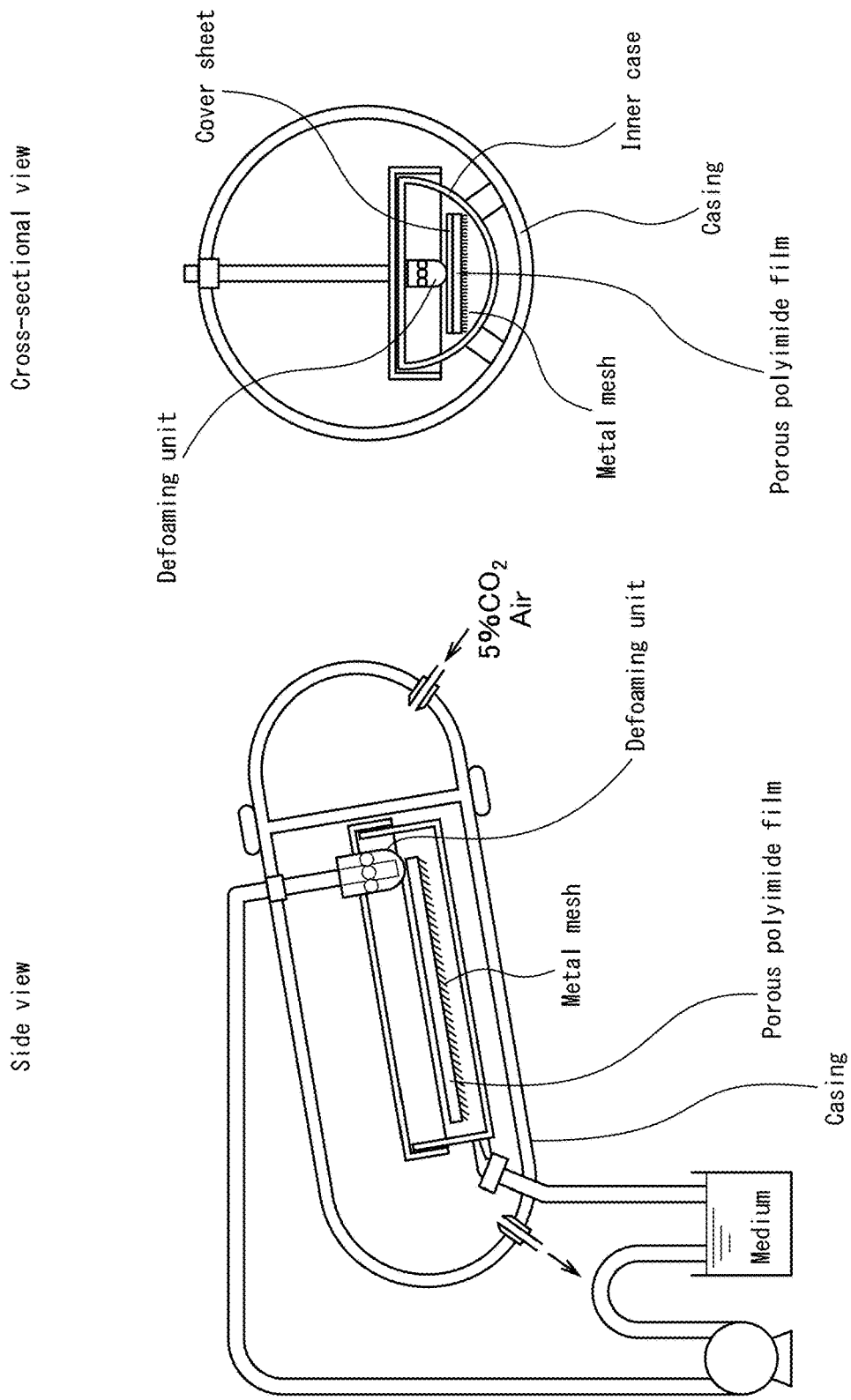
FIG. 2 shows an example of a cell culturing apparatus.

An example of a cell culturing apparatus, as a cell culturing system, is shown in FIG. 2, although the cell culturing system to be used for the object of the invention is not limited to such an apparatus.

II. Cell Culturing Apparatus

The present invention also relates to a cell culturing apparatus for use in the culturing method of the invention, the apparatus including a porous polyimide film. In the cell culturing apparatus of the invention, the porous polyimide film may be used in a fixed state, or it may be used in a floating state in the cell culture medium, and it may be either placed in the medium or exposed from the medium. In the cell culturing apparatus, two or more porous polyimide films may be layered either above and below or left and right. The layered aggregates or cluster may be either placed in the medium or exposed from the medium.

The cell culturing apparatus of the invention may be in any desired form so long as it includes the porous polyimide film. For example, any of the aforementioned cell culturing systems to be used for the long term culturing method of the invention may be used as the cell culturing apparatus for the invention.

III. Kit for Use in Cell Culturing Method

The present invention also relates to a kit for use in the cell culturing method of the invention, the apparatus including a porous polyimide film.

The kit of the invention may include constituent elements necessary for cell culturing in addition to the porous polyimide film, as appropriate. This includes, for example, the cells to be applied to the porous polyimide film, the cell culture medium, the continuous culture medium-supply apparatus, the continuous culture medium-circulating apparatus, the scaffold or module for support of the porous polyimide film, the cell culturing apparatus, and the kit instruction manual.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

IV. Use

The invention also relates to the use of a porous polyimide film for a long term cell culturing method. It still further relates to the use of the aforementioned cell culturing apparatus for a long term cell culturing method.

V. Cell Cryopreservation Method

The present invention relates to a cell cryopreservation method including:

(1) a step of supporting cells on a porous polyimide film, (2) a step of placing the cell-supporting porous polyimide film under conditions in which the cells freeze, to freeze the cells supported on the porous polyimide film, and (3) a step of storing the cell-supporting porous polyimide film under conditions in which the frozen state is maintained. According to the invention, the porous polyimide film can be frozen while supporting cells that have been cultured at high density, thereby allowing the cells to be frozen in an overwhelmingly higher density state than in conventional cell freezing methods in which freezing is in a non-adhered state.

1. Cells

There are no particular restrictions on the type of cells that can be utilized for the method of the invention, and any of the aforementioned cells may be used.

2. Step of Supporting Cells on Porous Polyimide Film

The method of the invention includes a step of supporting cells on a porous polyimide film.

Although any desired method may be used as the method of supporting the cells on the porous polyimide film, the following method may be used as an example.

(A) A mode including a step of seeding cells on the surface of the porous polyimide film;

(B) A mode including a step of placing a cell suspension on the dried surface of the porous polyimide film, allowing it to stand, or moving the porous polyimide film to promote liquid effusion, or stimulating part of the surface to cause absorption of the cell suspension into the film, and retaining the cells in the cell suspension inside the film and causing effusion of the water; and (C) a mode including a step of wetting one or both sides of the porous polyimide film with a cell culture medium solution or a sterilized liquid, loading a cell suspension into the wetted porous polyimide film, and retaining the cells in the cell suspension inside the film and causing effusion of the water.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

One or more separate non-cell-supporting porous polyimide films may be applied onto the same cell culture medium together with the cell-supporting porous polyimide film, and cultured to support the cells on the one or more separate porous polyimide films. During this procedure, the cell-supporting porous polyimide film and the one or more separate non-cell-supporting porous polyimide films may be in mutual contact by layering or the like, or they may be simply set in the same cell culture medium.

3. Step of Placing Cell-Supporting Porous Polyimide Film Under Conditions in which Cells Freeze, to Freeze Cells Supported on the Porous Polyimide Film The conditions under which the cells freeze may be set as appropriate so long as they are conditions under which some or all of the cells supported on the porous polyimide film maintain their biological function when thawed after freezing. A commercially available product may also be used, such as a freezing tube or freezing cane for placement in the porous polyimide film.

For example, the porous polyimide film may be immersed in a cell cryopreservation liquid and frozen under first low temperature conditions, and then transferred to and frozen under second low temperature conditions that are lower than the first low temperature conditions. The first low temperature conditions may be conditions of about minus 20 to 25° C., for example, and the second low temperature conditions may be conditions of about minus 80 to 90° C.

The step of placement under the first low temperature conditions may also be omitted. Switching to the second low temperature conditions that are lower than the first low temperature conditions may be in a linear, stepwise, curvilinear or immediate manner.

The apparatus that provides the first low temperature conditions and the apparatus that provides the second low temperature conditions may be separate apparatuses or the same apparatus. When the apparatus that provides the first low temperature conditions and the apparatus that provides the second low temperature conditions are separate apparatuses, they may be, for example, a common freezer as the apparatus that provides the first low temperature conditions and a deep freezer as the apparatus that provides the second low temperature conditions, though this is not restrictive. When the apparatus that provides the first low temperature conditions and the apparatus that provides the second low temperature conditions are the same apparatus, there may be used a programmed freezer that can lower the temperature at a fixed rate (for example, a programmed freezer by Nepa Gene Co., Ltd.), though this is not restrictive.

The cell cryopreservation liquid may be a publicly known one, used as appropriate. For example, it is suitable to use a cell culture solution with addition of DMSO at about 5% to 20%, a cell culture solution with addition of glycerol at about 5% to 20%, or a commercially available cell cryopreservation liquid such as the CELLBANKER series listed in the company catalog of ZENOAQ.

4. Step of Storing Cell-Supporting Porous Polyimide Film Under Conditions in which Frozen State is Maintained The method of the invention includes a step of storing the cell-supporting porous polyimide film under conditions in which the frozen state is maintained, as described above. The conditions in which the frozen state is maintained may be conditions of storage under the second low temperature conditions mentioned above, or conditions of storage under third low temperature conditions that are even lower than the second low temperature conditions. An example of the third low temperature conditions may be storage in liquid nitrogen, for example, though this is not a restriction.

In the method of the invention, any type of cells, whether suspension cells or adherent cells, can be satisfactorily cryopreserved. When suspension cells have been cryopreserved by the method of the invention, the cells are housed and stored in the spatial structure of the porous polyimide film while maintaining their spherical forms. When adherent cells have been cryopreserved by the method of the invention, the cells are housed and stored in the spatial structure of the porous polyimide film while maintaining their same non-spherical forms as during growth and proliferation in the porous polyimide film.

Naturally, the porous polyimide film supporting cells by the method of the invention is preferably in a state including no cells other than those supported, i.e. a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a disinfectant such as ethanol, or electromagnetic wave sterilization using ultraviolet rays or gamma rays.

5. Step of Thawing Cells Supported on Porous Polyimide Film

In the method of the invention, the cell-supporting porous polyimide film can be thawed after cryopreservation. The method of thawing the cells supported on the porous polyimide film may be a method of thawing by heating the cryopreserved porous polyimide film from outside of the storage vessel. The heating method may be a method of immersing the vessel in warm water at a constant temperature of about 37° C., as appropriate.

6. Step of Applying Cell-Thawed Porous Polyimide Film to Cell Culture Medium and Culturing Cells In the method of the invention, the cell-thawed porous polyimide film may be applied directly to a cell culture medium to culture the thawed cells on the same porous polyimide film.

The cells may be cultured until the cultured cells proliferate even outside of the porous polyimide film.

In the case of suspension cells, the cells that have migrated from inside the porous polyimide film into the cell culture medium can continue to proliferate in the medium. While adherent cells will usually stop within the porous polyimide film or on its surface, some of the cells can migrate to a culturing vessel contacting the porous polyimide film or to a separate culture support that is not supporting cells.

Thus, one or more separate non-cell-supporting porous polyimide films may be applied onto the cell culture medium together with the cell-thawed porous polyimide film, and cultured to support the cells on the one or more separate porous polyimide films, and culturing continued as necessary.

In this case, all or a portion of the cell-thawed porous polyimide film, and a separate porous polyimide film with newly supported cells, may be placed under conditions in which the cells freeze, to allow freezing and storage of the cells supported on the porous polyimide film.

The aforementioned steps of freezing, storage, thawing and culturing may be repeated several times. According to the invention, the porous polyimide film may be frozen and stored while supporting large volumes of cells, and thawed at an arbitrary time, to be used for desired purposes (for example, protein production), without requiring a pre-culturing step. For use of thawed cells in the prior art, it has been necessary to preculture the thawed cells and then culture the surviving cells after supporting them on a desired base material or support. According to the invention, however, it is possible to carry out culturing, freezing, storage, thawing and re-culturing of cells while they are adhering to the porous polyimide film, without a preculturing step after thawing as has been required in the prior art. Therefore, by preparing large amounts of a frozen cell-supporting porous polyimide film, large volumes of cells can be used at any desired time without an amplifying culturing step.

VI. Porous Polyimide Film for Cryopreservation of Cells

The invention also relates to a porous polyimide film for cryopreservation of cells. The porous polyimide film for cryopreservation of cells according to the invention may be a porous polyimide film for the cell cryopreservation method described above.

VII. Kit

The invention further relates to a kit for cryopreservation of cells, that includes a porous polyimide film.

The kit of the invention may include constituent elements necessary for cell culturing in addition to the porous polyimide film, as appropriate. For example, it may include a porous polyimide film, a cell cryopreservation liquid, a freezing tube, a freezing cane and a kit instruction manual.

While not restrictive, one mode includes a package containing either one or a plurality of sterilized porous polyimide films stored in a transparent pouch, in a form allowing their use for cell freezing, or a kit having a cryopreservation liquid encapsulated together with a porous polyimide film in the same pouch, in the form of an integrated film/liquid that can be rapidly used.

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 µm and a porosity of 73%. Each porous polyimide film had at least two different surface layers (A-surface and B-surface), and a macro-void layer sandwiched between the two surface layers. The mean pore size of the holes in the A-surface was 6 µm, and the mean pore size of the holes in the B-surface was 46 µm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

<Cells and Materials Used>

Human fibroblasts (product code CC-2511 by Lonza)
Vero cells (cat. DSIU002 by DS Pharma Biomedical Co., Ltd.)
CHO-K1 (cat. 85051005 by Public Health England)
CHO DP-12 (Summit Pharmaceuticals Intl, CRL-12445)
Human fibroblast medium (product code CC-3132 by Lonza)
Vero cell medium (E-MEM 051-07615, by Wako Pure Chemical Industries, Ltd.)
CHO-K1 medium (Ham's F-12 087-08335 by Wako Pure Chemical Industries, Ltd.)
CHO DP-12 medium (IMDM-06465 by Wako Pure Chemical Industries, Ltd.)
3.5 cm plate (cat. 353001 by Falcon)
Cell Counting Kit 8 (CCK8 CK04, Dojindo Laboratories)
Cryotube (1.8 ml cat. 377267 by Thermo Fisher Scientific)
2 cm×2 cm sterilized square vessel (cat. 103k by Thermo Fisher Scientific)
CELLBANKER (CELLBANKER 1 Plus cat. CB021 by Zenoaq)
Microscope, imaging software (LSM 700, ZEN software, by Carl Zeiss)

Example 1

Long Term Culturing of Human Skin Fibroblasts Using Porous Polyimide Film

Figure 3:
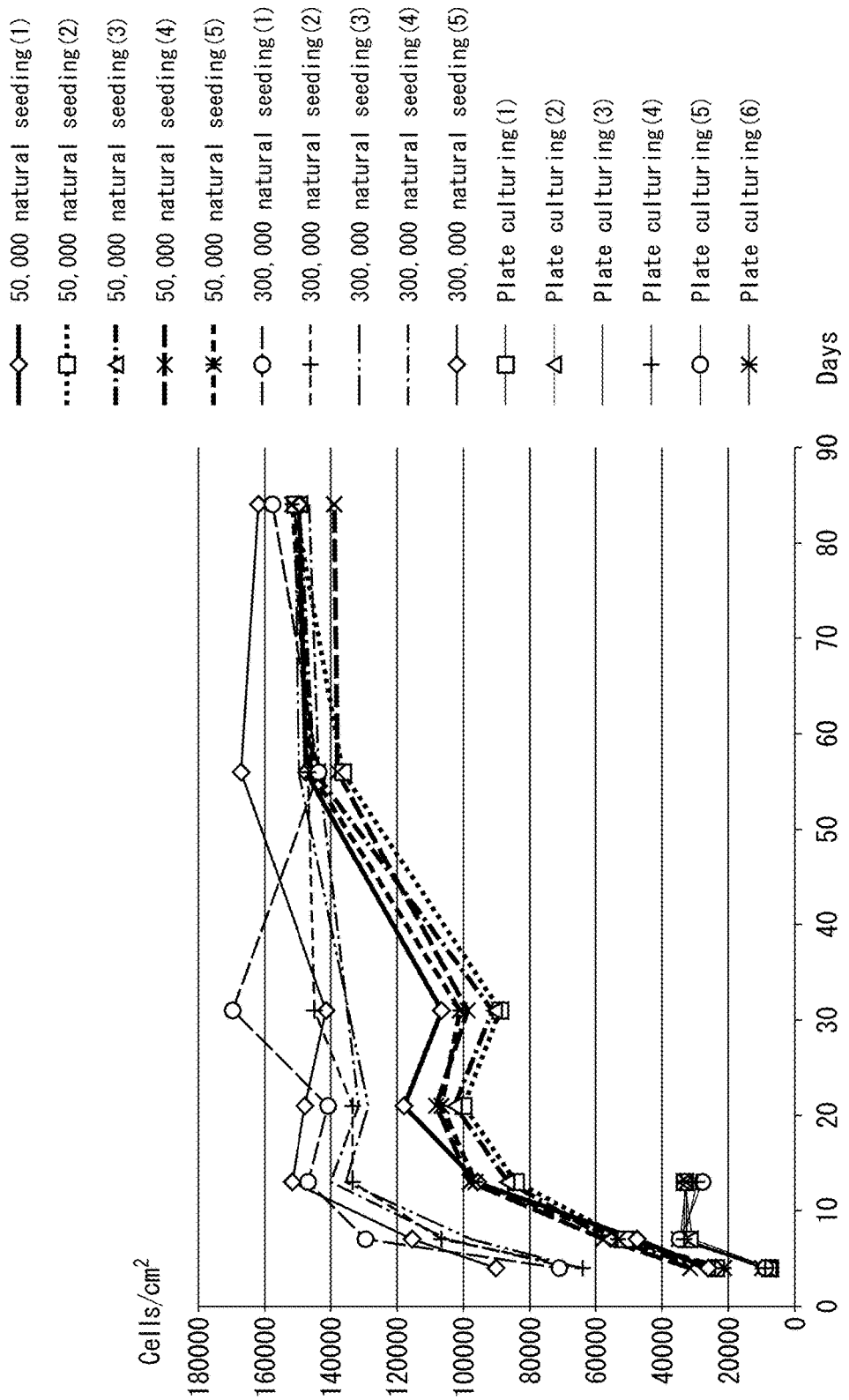
FIG. 3 shows results for long term culturing of human skin fibroblasts using a porous polyimide film.

After adding 0.5 ml of cell culture medium to a 2 cm×2 cm sterilized square vessel, each sterilized 1.4 cm-square porous polyimide film was immersed therein with the A-surface of the mesh structure or the B-surface of the large-hole structure facing upward. After then adding a suspension of $5 \times 10^4$ human skin fibroblasts per sheet or $3 \times 10^5$ human skin fibroblasts per sheet, cell culturing was carried out continuously while exchanging the medium at a frequency of twice per week. Five sheets of each were prepared and transferred to a 20 cm² plate, 4 ml of medium was added, and culturing was continued. After 4 days, 7 days, 13 days, 31 days, 56 days and 84 days, a CCK8 was used to measure the cell counts, and the growth behavior was observed. The results are shown in FIG. 3. For reference, the progress with plate culturing (seeding density: $3.5 \times 10^3/\text{cm}^2$) up to 14 days was also recorded.

Example 2

Long Term Culturing of Human Skin Fibroblasts Using Porous Polyimide Film

Figure 4:
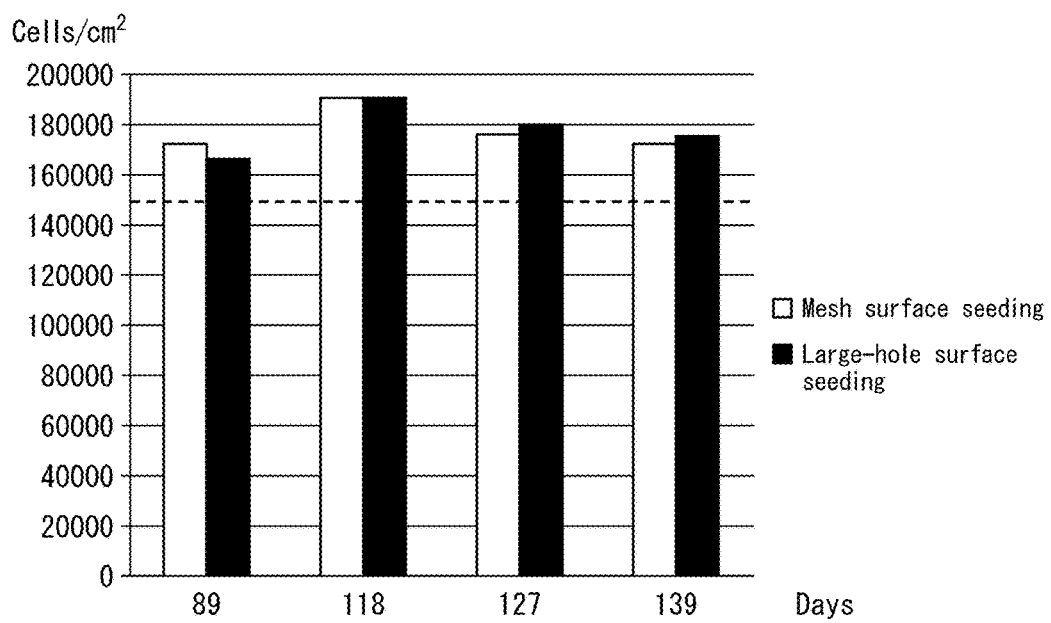
FIG. 4 shows results for long term culturing of human skin fibroblasts using a porous polyimide film.

After adding 0.5 ml of cell culture medium to a 2 cm×2 cm sterilized square vessel, a sterilized 1.4 cm-square porous polyimide film was dipped therein with the A-surface of the mesh structure or the B-surface of the large-hole structure facing upward. After then seeding $4 \times 10^4$ cells per sheet, cell culturing was continuously carried out in a $CO_2$ incubator. The medium (1 ml) was exchanged twice per week. After 89 days, 118 days, 127 days and 139 days from the start of culturing, a CCK8 was used to measure the cell counts, and the growth behavior of the cells was observed. Cell counts of $\geq 1.5 \times 10^5$ per 1 cm² were observed throughout the observation period. The results are shown in FIG. 4.

Example 3

Long Term Culturing of Vero Cells Using Porous Polyimide Film

Figure 5:
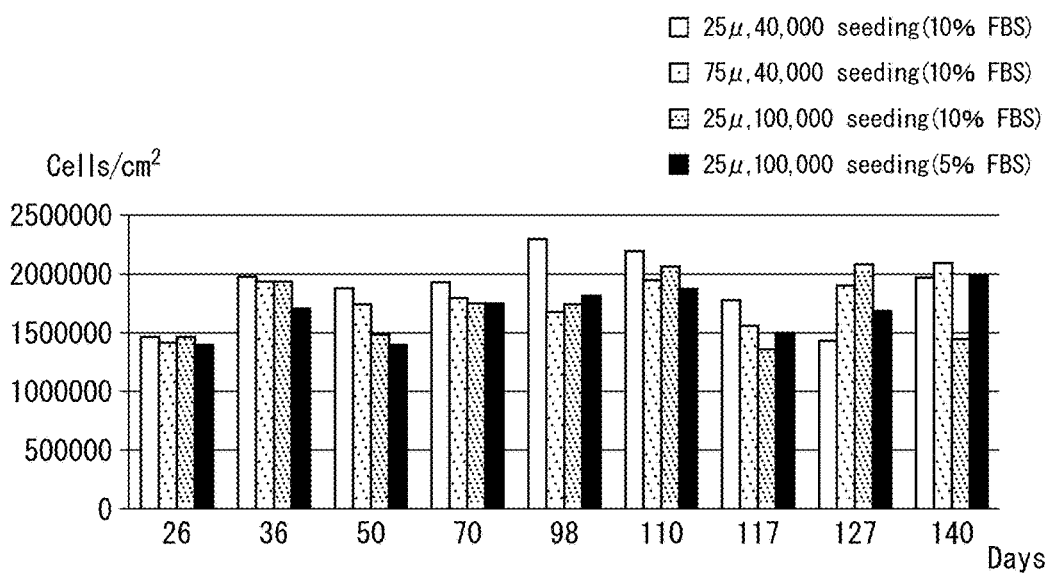
FIG. 5 shows results for long term culturing of Vero cells using a porous polyimide film.
Figure 6:
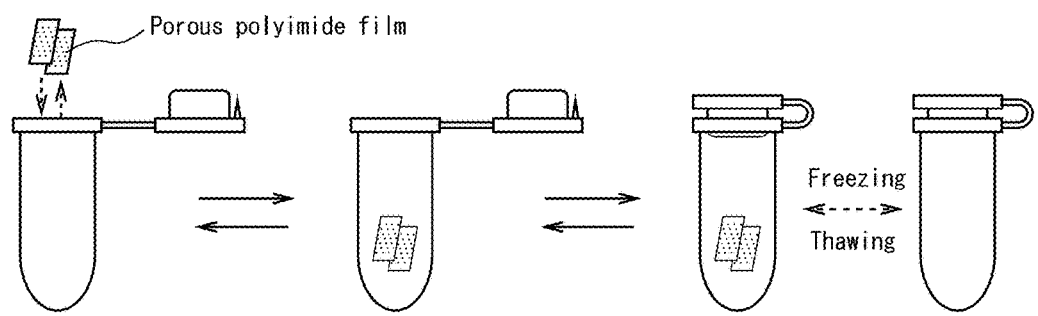
FIG. 6 is a conceptual drawing of the steps of cell freezing and thawing using a porous polyimide film. Unlike the freezing and thawing process for a cell suspension, the cell aggregate can be handled directly as a porous polyimide film, so that steps such as centrifugal separation can be completely eliminated.
Figure 7:
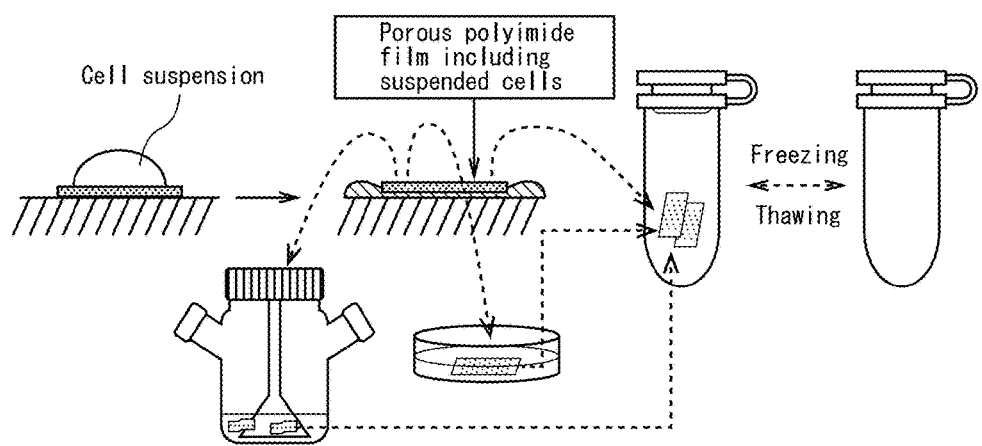
FIG. 7 is a conceptual drawing relating to freezing and thawing of suspension cells, and their utilization, using a porous polyimide film. Suspension cells have an advantage in that their property of overflowing from the porous polyimide film during the course of proliferation can be utilized, for their repeated use as a sample.

After adding 1 ml of cell culture medium to a 2 cm×2 cm sterilized square vessel, a sterilized 1.4 cm-square porous polyimide film was dipped therein with the A-surface of the mesh structure or the B-surface of the large-hole structure facing upward. After then seeding $4 \times 10^4$ and $1 \times 10^5$ cells per sheet, cell culturing was continuously carried out in a $CO_2$ incubator. Here, a 75 µm porous polyimide film was used in addition to a commonly used 25 µm-thick porous polyimide film. The amount of FBS used was 10% or 5% with respect to the medium. Culturing was continued with exchange of the medium (1 ml) twice per week. During the period of 140 days, a CCK8 was used for intermittent measurement of the cell count, and the growth behavior of the cells was observed. Stable cell growth was observed. The results are shown in FIG. 5.

Example 4

After adding 1 ml of cell culture medium to a 2 cm×2 cm sterilized square vessel, a 1.4 cm-square sterilized porous polyimide film was immersed therein with the A-surface of the mesh structure facing upward. After adding $4 \times 10^4$ CHO-K1 cells per sheet and culturing for 20 days, a CCK8 was used to measure the cell count, by which a cell count of $7.7 \times 10^6$ on the sheet was obtained.

The sheet on which the cells were growing was cut into 3 long sheets, and after storage for 20 hours at 5° C. while in the medium, the porous polyimide film was removed out and placed in a cryotube containing 1 ml of CELL-BANKER, stored at −20° C. for 24 hours, and then stored at −80° C. for 24 hours and transferred into liquid nitrogen. After 20 days, the tube was warmed to 37° C. to thaw the contents, and allowed to stand for 16 hours in an incubator. A CCK8 was used to measure the cell count, by which a cell count of $4.6 \times 10^6$ on the sheet was obtained.

Example 5

After adding 1 ml of cell culture medium to a 2 cm×2 cm sterilized square vessel, a 1.4 cm-square sterilized porous polyimide film was immersed therein with the A-surface of the mesh structure facing upward. After adding $4 \times 10^4$ human skin fibroblasts per sheet and culturing for 5 days, a CCK8 was used to measure the cell count, by which a cell count of $7.7 \times 10^6$ on the sheet was obtained.

The sheet on which the cells were growing was cut into 3 long sheets, and after storage for 8 hours at 5° C. while in the medium, the porous polyimide film was removed out and placed in a cryotube containing 1 ml of CELLBANKER, stored at −80° C. for 24 hours, and transferred into liquid nitrogen. After 2 days, the tube was warmed to 37° C. to thaw the contents, and transferred to culturing conditions in an incubator. After 3 days and 5 days, a CCK8 was used to measure the specific activity based on absorbance, by which specific activities of 36% and 64% were obtained for the 3rd day and 5th day, respectively.

Example 6

Figure 8:
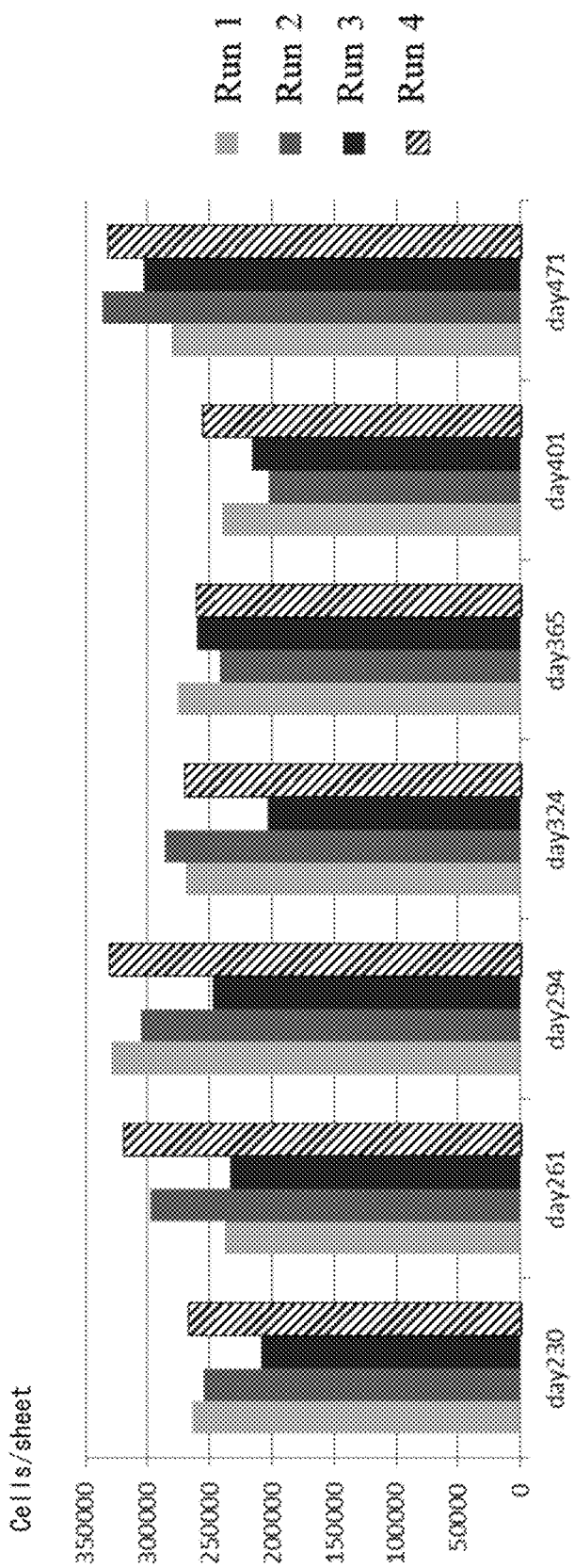
FIG. 8 shows results for long term culturing of human skin fibroblasts using a porous polyimide film.

Long Term Culturing of Human Skin Fibroblasts
Long Term Culturing of Human Skin Fibroblasts Using Porous Polyimide Film After adding 0.5 ml of 2% FBS-containing cell culture medium to a 2 cm×2 cm sterilized square vessel, each sterilized 1.4 cm-square porous polyimide film was dipped therein with the A-surface of the mesh structure facing upward. After then adding $4 \times 10^4$ of a human skin fibroblast suspension to each of the sheets, cell culturing was carried out continuously while exchanging the medium at a frequency of twice per week. After 231 days, 261 days, 294 days, 324 days, 365 days, 401 days and 471 days, a CCK8 was used to measure the cell counts, and the growth behavior was observed. The results are shown in FIG. 8. Stable viable cell counts were confirmed throughout the culturing period.

Example 7

Figure 9:
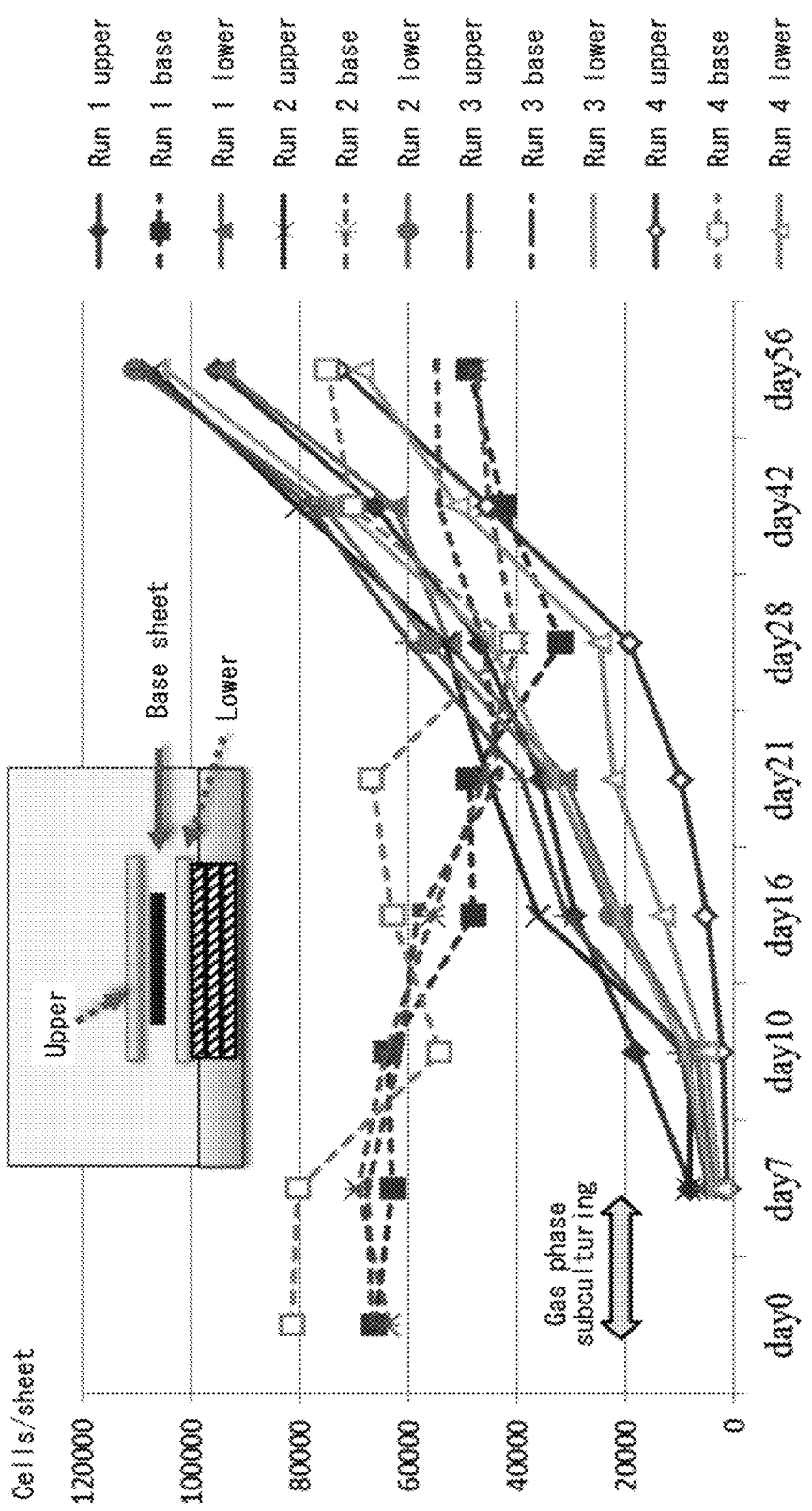
FIG. 9 shows results for long term culturing of human skin fibroblasts using a porous polyimide film.

Confirming Proliferation by Gas Phase Subculturing During Long Term Culturing of Human Skin Fibroblasts After adding 2 ml of 2% FBS-containing medium to a 6 cm-diameter plate, human skin fibroblasts were seeded on the A-surfaces of the mesh structures of 1.4 cm-square sterilized porous polyimide films, at $4 \times 10^4$ cells per sheet, and culturing was carried out for 1 month. The sheets were then cut into quarter portions and culturing was continued for a total of 230 days of culturing. Next, three 1.4 cm-square stainless steel meshes were stacked and set at the center of a 3.5 cm dish, and the porous polyimide film was placed thereover and sandwiched with two empty 1.4 cm-square sterilized porous polyimide films. When 1 ml of medium was added in this state, the medium reached approximately the height of the sheets. They were then directly moved into a $CO_2$ incubator, the medium was exchanged at a frequency of twice per week, and cell culturing was subsequently continued. After 7 days of culturing, each sheet was separately isolated and culturing was continued in each sheet. After 7, 10, 16, 21, 28, 42 and 56 days the cell counts were measured using a CCK8, and the cell growth behaviors on the original sheets and the subsequently set empty porous polyimide films were observed with a CCK8, based on staining. The behavior was observed whereby the cells efficiently migrated from the porous polyimide films in which long term culturing of human skin fibroblasts had taken place, to the empty porous polyimide films, and continuously proliferated. The results are shown in FIG. 9.

Example 8

Cell Culturing, Freezing and Substance Production Using CHO DP-12 Cells

After adding 0.5 ml of cell culture medium (2% FBS, IMDM, product of Wako Pure Chemical Industries, Ltd.) to a 2 cm×2 cm square sterilized vessel, each sterilized 1.4 cm-square porous polyimide film was immersed therein with the A-surface of the mesh structure facing upward. A human anti-IL-8 antibody-producing CHO DP-12 cell suspension was added to the sheets in each medium at $4 \times 10^4$ cells per sheet, and continuous cell culturing was carried out, with medium exchange at a frequency of twice a week. After cell culturing for 78 days, a CCK8 was used to measure the cell count.

Figure 10:
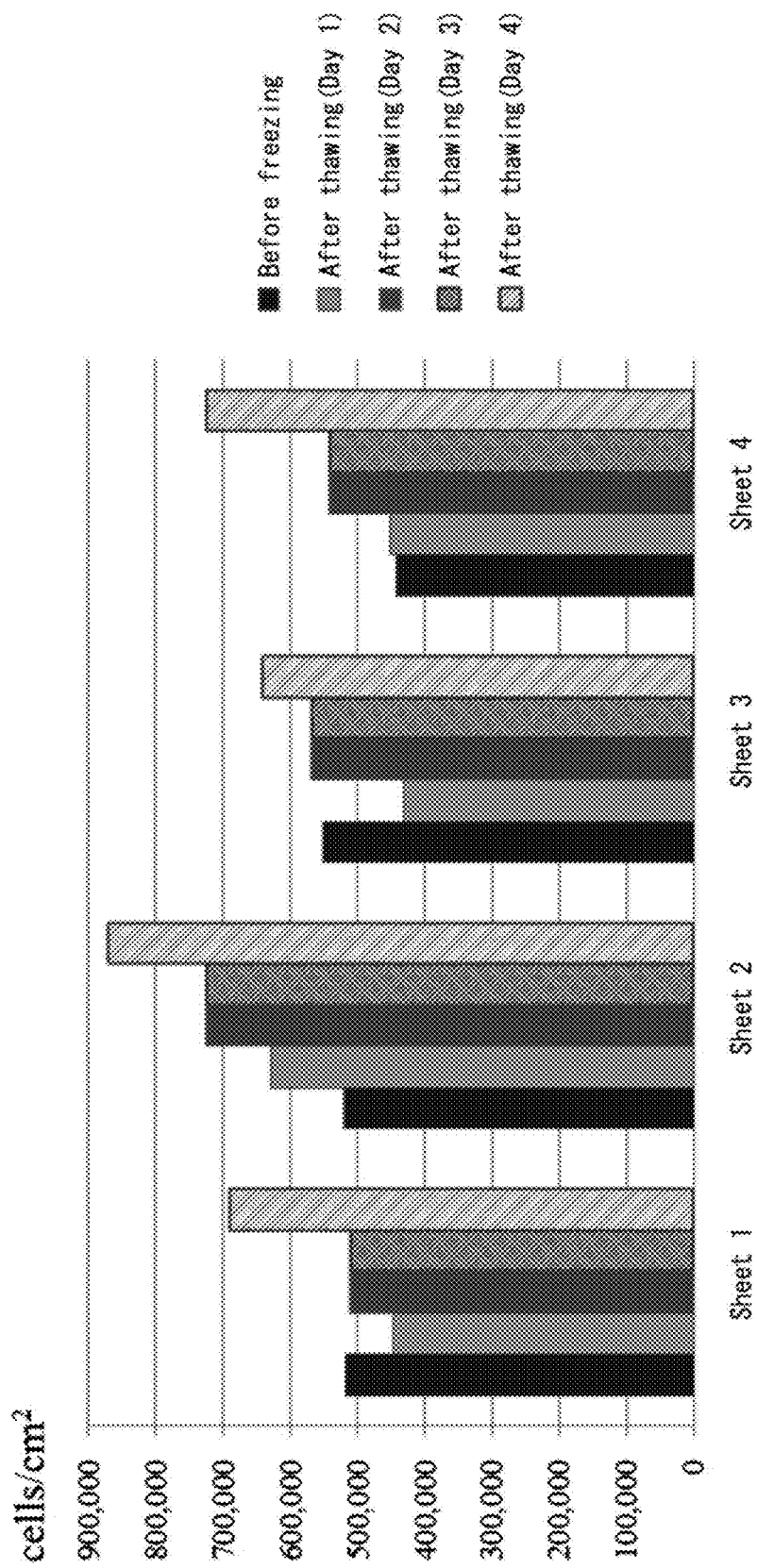
FIG. 10 shows results for freezing and then thawing and culturing of CHO DP-12 cells using a porous polyimide film.

Four of the sheets were transferred into 4 cryopreservation bags under sterile conditions at one sheet per bag, and 3 ml of CELLBANKER was added to each bag. After freezing with a programmed freezer at −80° C. under two different conditions (1° C. per minute or 1° C. every 10 minutes), it was stored at −80° C. for 24 hours and transferred into liquid nitrogen. After 3 days, each bag was heated to 37° C. to thaw the contents, and the sheets were transferred to four previously prepared 10 $cm^2$ plates filled with 2 ml of medium and allowed to stand in an incubator for 24 hours. Next, each sheet was transferred to a sterilized 2 cm×2 cm square vessel, 1 ml of cell culture medium was added, and culturing was carried out for another 3 days. After 24 hours, 2 days, 3 days and 4 days, a CCK8 was used to measure the cell counts. The results are shown in FIG. 10.

Two non-frozen sheets that had been seeded and continuously cultured at the same time and in the same manner as the four cell-cultured frozen sheets, were each placed in a 10 $cm^2$ plate, 2 ml of cell culture medium was added to each, and incubation was performed for 24 hours at 37° C. with 5% $CO_2$, after which the medium supernatants were recovered. The anti-human IL-8 antibody amounts in the recovered supernatants were quantified by ELISA. As shown in Table 2, no change in anti-IL-8 production was seen due to the freezing. The results are shown in Table 2.

TABLE 2

| | Anti-human IL-8 antibody (pg/cell/day) |
|---|---|
| Frozen sheet (1) | 26.4 |
| Frozen sheet (2) | 18.0 |
| Frozen sheet (3) | 24.0 |
| Frozen sheet (4) | 28.7 |
| Non-frozen sheet (1) | 16.2 |
| Non-frozen sheet (2) | 19.3 |

Example 9

Freezing of Human Skin Fibroblasts and Substance Production

After adding 0.5 ml of cell culture medium to a 2 cm×2 cm square sterilized vessel, 1.4 cm-square sterilized porous polyimide films were immersed therein with the A-surfaces of the mesh structure facing upward. After adding a suspension of $4\times10^4$ human skin fibroblasts per sheet onto the sheets in the medium, culturing was initiated in a $CO_2$ incubator. Cell culturing was continued with exchange of medium at a frequency of twice per week, and after cell culturing for 49 days, a CCK8 was used to measure the cell count, which was $9.1\times10^4$.

The cell-growing sheets were removed out of the medium and each was transferred to a previously prepared cryopreservation bag containing 3 ml of CELLBANKER, and after freezing to −80° C. in a programmed freezer, by lowering the temperature 1° C. every 10 minutes, it was stored at −80° C. for 24 hours and then stored in liquid nitrogen. After 5 days, the bag was heated to 37° C. to thaw the contents, and the sheets alone were transferred to a previously prepared 10 cm² plate filled with 2 ml of medium and continuously cultured in a $CO_2$ incubator. Medium exchange was performed at a pace of twice per week. After 24 hours, 5 days, 8 days, 13 days, 21 days, 29 days and 35 days, a CCK8 was used to measure the viable cell counts in the sheets. The results are shown in FIG. 11. After 24 hours, 8 days, 21 days and 35 days, the specific activity was found to be 34%, 91%, 105% and 152%, respectively. After culturing for 35 days, the amount of fibronectin production by the human skin fibroblasts growing on the same sheet was measured by ELISA. The results are shown in the following table. There was no damage by the freezing, and continuous substance production was confirmed. The results are shown in Table 3.

TABLE 3

| Entry (days cultured and condition) | Fibronectin production per unit area (ng/cm²/day) |
|---|---|
| Porous polyimide film, normal culturing, day 13 (Run 1) | 480 |
| Porous polyimide film, normal culturing, day 13 (Run 2) | 376 |
| Sheet cultured for 35 days after freezing/thawing | 685 |

What is claimed is:

1. A cell cryopreservation method, including:
   (1) a step of supporting cells on a porous polyimide film,
   (2) a step of placing the cell-supporting porous polyimide film under conditions in which the cells freeze, to freeze the cells supported on the porous polyimide film, and
   (3) a step of storing the cell-supporting porous polyimide film under conditions in which the frozen state is maintained,
   wherein the porous polyimide film with a multilayer structure, having at least two surface layers (an A-surface and a B-surface), and a macro-void layer sandwiched between the two surface layers,
   a mean pore size of the holes in the A-surface is smaller than a mean pore size of the holes in the B-surface, and the macro-void layer has a partition bonded to the surface layers (the A-surface and the B-surface), and a plurality of macro-voids surrounded by the partition and the surface layers (the A-surface and the B-surface).

2. The method according to claim 1, wherein in step (1), the cells are seeded on the porous polyimide film to support the cells on the porous polyimide film.

3. The method according to claim 1, wherein in step (1), the cells are seeded and cultured on the porous polyimide film to support the cells on the porous polyimide film.

4. The method according to claim 1, which further includes, following step (3),
   (4) a step of placing the cell-supporting porous polyimide film under conditions in which the cells thaw, to thaw the cells supported on the porous polyimide film.

5. The method according to claim 4, which further includes, following step (4),
   (5) a step of applying the cell-thawed porous polyimide film to a cell culture medium and culturing the cells.

6. The method according to claim 5, wherein in step (5), the cells are cultured until the cultured cells proliferate even outside of the porous polyimide film.

7. The method according to claim 5, wherein in step (5), the one or more separate non-cell-supporting porous polyimide films are applied onto the cell culture medium together with the cell-thawed porous polyimide film, and culturing is carried out to support the cells on the one or more separate porous polyimide films.

8. The method according to claim 5, which further includes, following step (5),
   (6) a step of placing all or a portion of the cell-supporting porous polyimide film under conditions in which the cells freeze, to freeze the cells supported on the porous polyimide film, and
   (7) a step of storing the cell-supporting porous polyimide film under conditions in which the frozen state is maintained.

9. The method according to claim 8, wherein steps (1) to (7) are repeated several times.

10. The method according to claim 1, wherein the cells are selected from the group consisting of animal cells, insect cells, plant cells, yeast cells and bacteria.

11. The method according to claim 10, wherein the animal cells are cells derived from an animal belonging to the subphylum Vertebrata.

12. The method according to claim 10, wherein the cells are adherent cells.

13. The method according to claim 10, wherein the cells are suspension cells.

14. The method according to claim 1, wherein the porous polyimide film is a porous polyimide film including a polyimide obtained from a tetracarboxylic dianhydride and a diamine.

15. The method according to claim 14, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

16. A kit for use in the method according to claim 1, including a porous polyimide film and a cell cryopreservation liquid, wherein the porous polyimide film with a multilayer structure, having at least two surface layers (an A-surface and a B-surface), and a macro-void layer sandwiched between the two surface layers, a mean pore size of the holes in the A-surface is smaller than a mean pore size of the holes in the B-surface, and the macro-void layer has a partition bonded to the surface layers (the A-surface and the B-surface), and a plurality of macro-voids surrounded by the partition and the surface layers (the A-surface and the B-surface).

* * * * *